United States Patent [19]

Schulz

[11] Patent Number: 4,841,786
[45] Date of Patent: Jun. 27, 1989

[54] SPECIMEN DISTRIBUTING SYSTEM

[75] Inventor: Peter Schulz, Ludwigsburg, Fed. Rep. of Germany

[73] Assignee: Forschungs-& Entwicklungs-KG, Ludwigsburg, Fed. Rep. of Germany

[21] Appl. No.: 202,393

[22] Filed: Jun. 6, 1988

[30] Foreign Application Priority Data

May 2, 1986 [DE] Fed. Rep. of Germany ....... 3614955

[51] Int. Cl.$^4$ ...................... B01L 3/02; G01N 35/00; G01N 1/10
[52] U.S. Cl. .................................. 73/864.25
[58] Field of Search ........... 73/864.01, 864.11, 864.12, 73/864.22, 864.24, 864.25, 864.31, 864.34, 864.35, 290 V; 422/64, 67, 100

[56] References Cited

U.S. PATENT DOCUMENTS

| | | | |
|---|---|---|---|
| 3,192,968 | 7/1965 | Baruch et al. | 73/864.24 |
| 3,687,632 | 8/1972 | Natelson | 73/864.25 |
| 3,788,816 | 1/1974 | Rohrbaugh et al. | 422/64 |
| 3,912,456 | 10/1975 | Young | 73/864.25 |
| 4,325,416 | 4/1982 | Hermann | 73/290 V |
| 4,341,736 | 7/1982 | Drbal et al. | 73/864.25 |
| 4,648,866 | 3/1987 | Malbrancq et al. | 604/5 |
| 4,675,301 | 6/1987 | Charneski et al. | 73/864.35 |

FOREIGN PATENT DOCUMENTS

| | | | |
|---|---|---|---|
| 0040928 | 12/1981 | European Pat. Off. | 73/864.35 |
| 3016294 | 10/1981 | Fed. Rep. of Germany | |
| 2239167 | 2/1975 | France | 73/864.25 |

Primary Examiner—Stewart J. Levy
Assistant Examiner—Robert R. Raevis
Attorney, Agent, or Firm—Thomas W. Speckman

[57] ABSTRACT

A specimen distributing system for the remote-controlled extraction of sample specimens is provided wherein manipulator units supporting pipettes are movable horizontally and vertically and specific quantities of sample fluids may be transferred from primary containers to secondary containers. The distributing system comprises a table unit which is rotatable around a central vertical axis, with secondary containers forming container assemblies arranged around the circumference of the table unit and positioned peripheral to the table unit. The distributing system furthermore comprises a washing device for the pipettes and a central control unit. Manipulator units are supported by the table unit, and distributed around the central axis, and primary containers forming a container assembly are positioned peripheral to the table unit. The washing station is arranged between the last secondary container and the primary container assembly.

11 Claims, 2 Drawing Sheets

SPECIMEN DISTRIBUTING SYSTEM

CROSS REFERENCE TO RELATED APPLICATION

This is a continuation application of Ser. No. 046,022, filed May 4, 1987 now abandoned.

BACKGROUND OF THE INVENTION

1. Field of the Invention

This invention relates to a specimen distributing system providing remote controlled distribution of specific quantities of fluids from primary containers, by means of manipulator units supporting pipettes which undergo horizontal and vertical movements, and transfer of the specimens into secondary containers. The specimen distribution system comprises a table unit which is preferably rotatable around a central vertical axis, with secondary containers arranged in container assemblies provided around the circumference of the table unit, a washing device for rinsing the pipettes, and a central control unit.

Specimen distributing systems of the type described above are used mainly in medical laboratories. In such laboratories, the samples are generally distributed to sections. A mechanized samples distributor is suitably employed only in the primary distribution of serum, plasma, liquids and urine to the various laboratory sections, and for the secondary distribution of large series of experimental results.

2. Description of the Prior Art

In known systems of the type described above, such as are taught, for example, in German Patent Publication DE-OS No. 30 16 294, devices are used to distribute liquid research specimen materials for the purpose of analysis, in which the research material is assembled in series of correspondingly designated individual extraction vessels, which are controlled and monitored by a calculator unit according to the job description, and may be transferred, in stages, on a movable support to a filling point with automatic pipetting devices. At this point, the samples to be examined may be emptied into rows of analysis vessels. The movable support for the extraction vessels may be provided with more than a single filling point, at which, during a single process involving a series of extraction vessels and automatic pipette devices, transfer of the samples may be carried out in various series of similar or different analysis vessels which are positioned at the corresponding filling point. These extraction vessels may include, for example, chains, racks, plates or rings. In known systems, primary containers are positioned on the table unit which undergoes rotational movements, while the secondary containers are positioned outside the table unit. In this manner, the samples may be, of course, distributed in a problem-free manner. However, the secondary containers with specimens, which are provided for the same experimental researches, are positioned at different points, so that these containers, before examination, must be combined together in a container assembly to carry out the experimental examination. Collecting and combining the secondary containers is not only complicated, but it also has the disadvantage that undesirable confusion of individual containers may occur. The possibility that secondary containers may be confused is by no means negligible.

Furthermore, the known device also has the disadvantage that the movement of the filling points and the pipettes cannot be optimized.

SUMMARY OF THE INVENTION

The objective of the present invention is to simplify the specimen distributing system so that the secondary containers provided for similar analyses are arranged in a common container assembly. It is an additional objective to minimize the movements of the pipettes in relation to the secondary containers, as well as the number of washing devices.

The objective is achieved in accordance with the present invention as follows: manipulator units are supported by a table unit and distributed around a central vertical axis of the table unit; primary and secondary containers are arranged in container assemblies which and are positioned outside the table unit; and the washing station is positioned between the last secondary container and the primary container assembly with respect to the rotational direction of the table unit.

An important feature of the invention is that not only the primary containers, but also the secondary containers, are positioned around the circumference of a table unit of the system, and the secondary containers are arranged according to the types of experiments. This provides the advantage that it is no longer necessary to combine secondary containers in which the same analyses are performed since the container assemblies are subdivided according to type of analysis. Thus, it is not possible to have a combination of individual containers. In accordance with the invention, the pipettes, on one hand, undergo circular movements about the axis, and, on the other hand, undergo tangential movements relative to these circular movements. Furthermore, the pipettes can also undergo vertical back and forth movements, which pipettes in the known distributing systems can also execute. Through this fact, and, due to the circular movement of the pipettes, it is possible to considerably reduce the number of washing devices necessary and, as a general rule, the system can dispense with providing a washing device for all the pipettes.

Further advantageous and suitable features of the invention will become apparent from the following description.

Through the fact that the distance of manipulator units from the central vertical axis of the table unit is equally great, and the pipettes can undergo linear back and forth movements in a horizontal plane, the distance which the pipette covers between the primary container and the secondary containers may be further reduced. In the specimen distribution systems of the present invention, each manipulator unit preferably has a vertically-oriented support with a horizontally-oriented cross piece, with the free ends of the cross-piece each supporting a pipette. The support is preferably movable back and forth on a guide oriented tangentially to the radius of the table unit, while the cross-piece is movable vertically back and forth on the support.

In this regard, it may be provided that the container assemblies are movable back and forth in a radial direction with respect to the table unit. In the specimen distributing systems in accordance with the present invention, manipulator units are therefore distributed around the central vertical axis of the table unit, so that even during the rotation by stages of the table unit about the axis, the pipettes and the secondary container assemblies may be moved synchronously. If, therefore, the table unit rotates about a specified angle, the pipettes are located above the secondary containers, so that the pipettes need only execute a vertical downwards motion, which may be likewise controlled.

As already indicated, pipettes are distributed uniformly around the axis. The sample distribution cycle of the present system is completed when all the samples have been distributed, and when all the pipettes have been washed and are ready for re-use as more fully explained in the next paragraphs.

The distribution is carried out individually as follows: samples are first identified and positioned in the primary container assembly. When the specimen distributing system is activated, the first sample is removed through a pipette which cooperates with the primary assembly. Next, the table unit is rotated around its central axis, specifically at an angle of $\alpha = 360/n$, n = number of pipettes. If, for example, in sample $P_1$, only analyses $U_i$ and $U_j$, with $1 \leq i = j \leq n$, with n = number of analyses, have been carried out, then only sample $P_1$ is pipetted at the stations $U_i$ and $U_j$. If the pipette with the first sample is positioned above a secondary container assembly, the internal coding of which is different from i and j, then no pipetting occurs. After distribution, the pipette undergoes treatment in the washing device for the next pipetting process. In this connection, it is preferable that the pipette cooperates with a vibration imparting device, which vibrates the end of the pipette, with the frequency of vibrations in the range of ultrasonic vibrations.

This type of cleaning process for the pipettes is not only economical of time, but also particularly effective, since the bacteria-free residues of the previous sample may be removed as well in this manner.

To optimize the vertical back-and-forth movements of the pipette, another preferred embodiment of this invention provides that the pipette cooperates with a vibration imparting device and a vibration receiving device, and that the control unit has a comparator which compares the ideal to the measured frequency of the end of the pipette. Sample tubes may be standardized in a known manner, so that not only the contents of the sample, but also the movement of the pipette may be calculated and stored by the control unit.

To reduce the down-time of the sample distributing system, one additional embodiment of this invention provides that each pipette is connected to a dilutor, the dilutors are positioned around the central axis of the table unit, and a pressure sensor is positioned between the tube connecting the pipette with the dilutor. By means of this pressure sensor, obstructions of the pipette may be determined and signalled in a particularly simple manner.

BRIEF DESCRIPTION OF THE DRAWINGS

One embodiment of the invention is depicted in the diagrams, and is described in greater detail in the following description. In the drawings.

DESCRIPTION OF PREFERRED EMBODIMENTS

Figure 1:
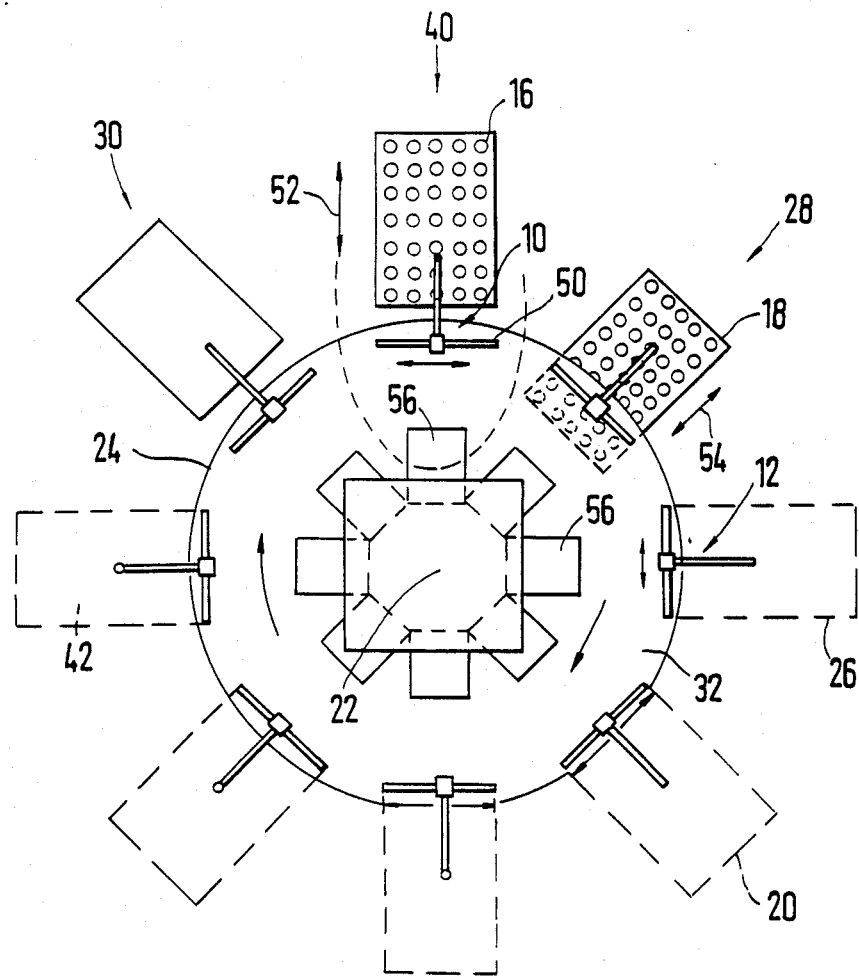
FIG. 1 shows a top view of a specimen distributing system, schematically represented.
Figure 2:
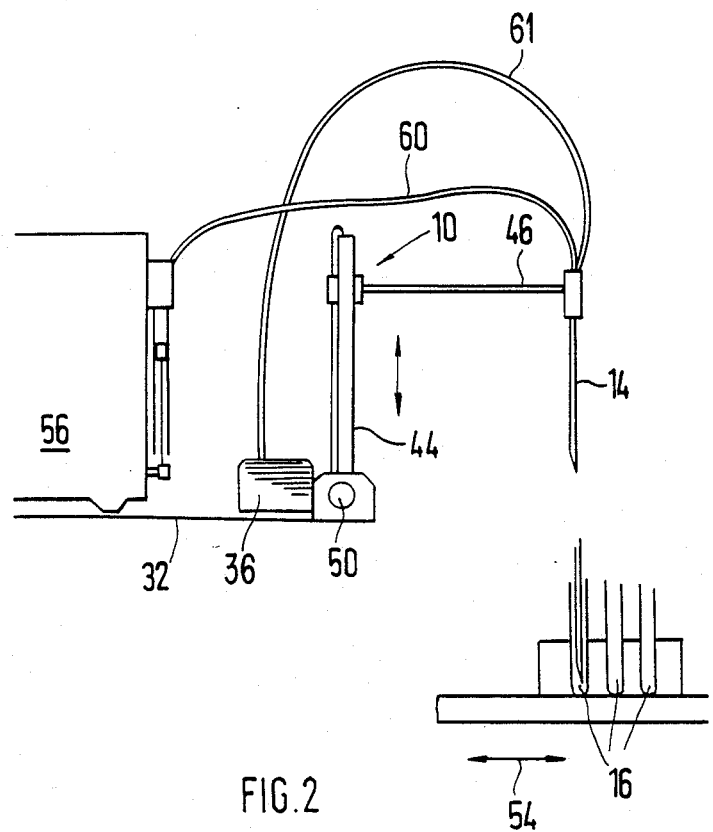
FIG. 2 shows, likewise in schematic representation, a side view of a manipulator unit with a pipette.

FIGS. 1 and 2 show a specimen distributing system providing remote controlled removal of specific quantities of fluids from primary containers (16), by means of manipulator units (10, 12), supporting pipettes (14) which undergo horizontal and vertical movements, and transfer of these into secondary containers (18, 20). The system comprises a table unit (32), which is preferably rotatable around a vertical axis (22), and around the circumference (24) of which secondary containers are provided and form container assemblies (26, 28) positioned outside the table. The specimen distributing system furthermore comprises a washing device (30) for pipettes (14), and a central control unit, which is not shown in detail.

Manipulator units (10) are supported on table unit (32), and are distributed around central vertical axis (22). Primary containers (16) are combined to form container assembly (40), and are positioned outside table unit (32). Washing station (30) is provided, considered from the clockwise rotational direction of table (32), between the last secondary container assembly (42), and primary container assembly (40). As shown in FIG. 1, the distance of manipulator units (10) from central vertical axis (22) is equal, and pipettes (14) undergo linear back-and-forth movements in a horizontal plane. Manipulator units (10) each have a vertically-oriented support (44), with a horizontally-oriented cross-piece (46), and the free ends of cross-pieces (46) each support a pipette (14). Vertical support (44) can move back and forth on guide (50) aligned perpendicular to the radius of table unit (32), while horizontal cross-piece (46) is vertically adjustable on support (44).

Container assemblies (28, 40) are movable in a radial direction with respect to the table, as shown by arrows (52, 54). Pipettes (14) may be connected to a dilutor (56), and dilutors (56) may be positioned around central axis (22) of table unit (32). The dilutor is a mechanical device for taking up a set quantity of specimen, and transferring it to a reaction tube tubelet, with the addition of a quantity of reagents from a reservoir. For example, 0.1 ml of sample may be removed and diluted with 1 ml of reagent. The dilutor device is preferably equipped with two injection devices for this purpose: the first withdraws the specimen, while the second withdraws reagent from the reservoir. The specimen is, in a second step, released by the pipette injection device, and, after adjustment of a value, the reagent is released as well. Since the reagent is generally released at an overflow level, a good rinsing effect of the pipette injection device takes place. In this embodiment, it is preferable to provide a pressure sensor (61) in connection with lead (60) connecting pipette (14) with dilutor (56), which is not illustrated in detail, to measure specific overpressure or underpressure in the line. If the expected pressure value is exceeded to a significant degree, then it may be assumed that the pipette has been obstructed with, for example, coagulate material.

Pipette (14) may, furthermore, cooperate with a vibration imparting device and a vibration receiving device (15), which are not illustrated in detail, whereby a comparator (36) provided in the control unit is in communication with the vibration receiving device via communication cable (61) and compares the ideal frequency with the actual frequency of the pipette end. By this means it can be determined in a simple manner whether or not the pipette end is already in contact with the specimen. This information that the end of the pipette is in contact with the specimen, may then be conveyed to the central control unit, then a calculator means may compute how deeply the pipette end must be inserted into the specimen to remove the desired quantity of specimen. In this manner, moistening of the pipette may be minimized.

Emergency specimens, such as rush analyses, must be tested immediately, so their immediate transfer to Primary containers of the specimens distributor is necessary. The specimens may be pipetted from Primary containers of the specimen distribution system at the beginning of the sequence into positions which have been kept available. The number of available positions for emergency specimens is something that each user can decide for himself.

The pipettes are preferably equipped with vibration imparting devices and vibration receiving devices, and to provide control of the insertion depth, to minimize the moistening of the removal pipette. At the final station, the pipettes are washed. At the washing station, the pipettes are rinsed with water while they penetrate a foil to clean the external wall of the pipette. The orderly positioning of the pipettes may also be checked here.

During distribution of the specimens in the analysis series, the necessary serum quantity, corresponding to the work list obtained from the laboratory computer, is pipetted into test vessels. Distribution normally takes place simultaneously from the original test tubes, for up to 8 analysis series. The specimens suctioned off are, if necessary, diluted with reagents or with water by dilutor means.

The object of the invention may be achieved if distribution of specimens takes place by having several manipulator units which can undergo circular movements and which can support pipettes that can move in a vertical direction and backward and forward in a tangential direction. To optimize the movement, it is preferable that the containers comprising container assemblies undergo back and forth movements.

Considered in general, a specimen distribution system is provided by this invention, in which both primary and secondary tubes are radially positioned, and whereby secondary tubes may be distributed in batches provided for various analyses. This invention therefore provides an extremely simple and understandable distribution of the tubes.

I claim:

1. A specimen distribution apparatus for automated extraction of specified quantities of sample specimens from primary containers and transfer of said sample specimens to secondary containers for testing, said apparatus comprising: a circular table rotatable about a central vertical axis; a plurality of manipulator units supported on said table and spaced a radial distance from said central vertical axis, each said manipulator unit movable back and forth in a linear direction perpendicular to the radius of said table and each said manipulator unit supporting at least one pipette movable in vertical direction; a plurality of said primary containers forming a primary container assembly, said primary container assembly radially arranged with respect to said central vertical axis, extending beyond the circumference of and radially movable with respect to said central vertical axis of said table; a plurality of said secondary containers forming secondary container assemblies, each said secondary container assembly arranged radially with respect to said central vertical axis, extending beyond said circumference of and radially movable with respect to said central vertical axis of said table and circumferentially aligned with said primary container assembly; and a washing device for cleaning said pipettes circumferentially aligned with said primary and said secondary container assemblies and between the last said secondary container assembly and said primary container assembly with respect to said rotatable direction of said table.

2. A specimen distributing apparatus in accordance with claim 1, characterized in that each said manipulator unit is spaced the same said radial distance from said central vertical axis.

3. A specimen distributing apparatus in accordance with claim 1, additionally comprising at least one dilutor means arranged on said table radially with respect to said central vertical axis.

4. A specimen distributing apparatus in accordance with claim 1, characterized in that a lead connects each said pipette to said at least one dilutor means, and a pressure sensor is provided in communication with said lead and said dilutor means.

5. A specimen distribution apparatus in accordance with claim 1, additionally comprising a vibration imparting device and a vibration sensing device in communication with each said pipette, and a comparator means which compares the nominal frequency to the measured frequency of the end of each said pipette.

6. A specimen distribution apparatus for automated extraction of specified quantities of sample specimens from primary containers and transfer of said sample specimens to secondary containers for testing, said apparatus comprising: a circular table rotatable about a central vertical axis; a plurality of manipulator units supported on said table and spaced the same radial distance from said central vertical axis, each said manipulator unit movable back and forth in a linear direction perpendicular to the radius of said table and each said manipulator unit supporting at least one pipette movable in vertical direction; a plurality of said primary containers forming a primary container assembly, said primary container assembly radially arranged with respect to said central vertical axis, extending beyond the circumference of and radially movable with respect to said central vertical axis of said table; a plurality of said secondary containers forming secondary container assemblies, each said secondary container assembly arranged radially with respect to said central vertical axis, extending beyond said circumference of and radially movable with respect to said central vertical axis of said table and circumferentially aligned with said primary container assembly; and a washing device for cleaning said pipettes circumferentially aligned with said primary and said secondary container assemblies and between the last said secondary container assembly and said primary container assembly with respect to said rotatable direction of said table, each said manipulator unit comprises a vertically oriented support with a horizontally oriented cross-piece extending beyond said circumference of said table over one of said container assemblies, said vertically oriented support is movable back and forth on a guide unit aligned perpendicular to the radius of said table, and said horizontally oriented cross-piece supports said at least one pipette and is vertically adjustable on said vertically oriented support.

7. A specimen distributing apparatus in accordance with claim 6, additionally comprising at least one dilutor means arranged on said table radially with respect to said central vertical axis.

8. A specimen distributing apparatus in accordance with claim 7, characterized in that a lead connects each said pipette to said at least one dilutor means, and a pressure sensor is provided in communication with said lead and said dilutor means.

9. A specimen distributing apparatus in accordance with claim 8, additionally comprising a vibration imparting device and a vibration sensing device in communication with each said pipette, and a comparator means which compares the nominal frequency to the measured frequency of the end of each said pipette.

10. A specimen distribution apparatus for automated extraction of specified quantities of sample specimens from primary containers and transfer of said sample specimens to secondary containers for testing, said apparatus comprising: a circular table rotatable about a central vertical axis; a plurality of manipulator units supported on said table and spaced a radial distance from said central vertical axis, each said manipulator unit movable back and forth in a linear direction perpendicular to the radius of said table and each said manipulator unit supporting at least one pipette movable in vertical direction; a plurality of said primary containers forming a primary container assembly, said primary container assembly radially arranged with respect to said central vertical axis, extending beyond the circumference of and radially movable with respect to said central vertical axis of said table; a plurality of said secondary containers forming secondary container assemblies, each said secondary container assembly arranged radially with respect to said central vertical axis, extending beyond said circumference of and radially movable with respect to said central vertical axis of said table and circumferentially aligned with said primary container assembly; and a washing device for cleaning said pipettes circumferentially aligned with said primary and said secondary container assemblies and between the last said secondary container assembly and said primary container assembly with respect to said rotatable direction of said table, each said manipulator unit comprises a vertically oriented support with a horizontally oriented cross-piece extending beyond said circumference of said table over one of said container assemblies, said vertically oriented support is movable back and forth on a guide unit aligned perpendicular to the radius of said table, and said horizontally oriented cross-piece supports said at least one pipette and is vertically adjustable on said vertically oriented support.

11. A specimen distribution apparatus for automated extraction of specified quantities of sample specimens from primary containers and transfer of said sample specimens to secondary containers for testing, said apparatus comprising: a circular table rotatable about a central vertical axis; a plurality of manipulator units supported on said table and spaced a radial distance from said central vertical axis, each said manipulator unit movable back and forth in a linear direction perpendicular to the radius of said table and each said manipulator unit supporting at least one pipette movable in vertical direction; a plurality of said primary containers forming a primary container assembly, said primary container assembly radially arranged with respect to said central vertical axis, extending beyond the circumference of and radially movable with respect to said central vertical axis of said table; a plurality of said secondary containers forming secondary container assemblies, each said secondary container assembly arranged radially with respect to said central vertical axis, extending beyond said circumference of and radially movable with respect to said central vertical axis of said table and circumferentially aligned with said primary container assembly, said primary and secondary container assemblies are movable in a radial direction with respect to said central vertical axis; and a washing device for cleaning said pipettes circumferentially aligned with said primary and said secondary container assemblies and between the last said secondary container assembly and said primary container assembly with respect to said rotatable direction of said table.

* * * * *